(12) United States Patent
Whelan

(10) Patent No.: US 9,619,039 B2
(45) Date of Patent: Apr. 11, 2017

(54) OBTAINING METRICS FOR A POSITION USING FRAMES CLASSIFIED BY AN ASSOCIATIVE MEMORY

(71) Applicant: The Boeing Company, Chicago, IL (US)

(72) Inventor: John Desmond Whelan, Burien, WA (US)

(73) Assignee: THE BOEING COMPANY, Chicago, IL (US)

( * ) Notice: Subject to any disclaimer, the term of this patent is extended or adjusted under 35 U.S.C. 154(b) by 55 days.

(21) Appl. No.: 14/478,475

(22) Filed: Sep. 5, 2014

(65) Prior Publication Data
US 2016/0070355 A1 Mar. 10, 2016

(51) Int. Cl.
| | |
|---|---|
| G06F 3/01 | (2006.01) |
| G06K 9/00 | (2006.01) |
| G06T 7/20 | (2006.01) |
| A61B 5/11 | (2006.01) |
| G06T 7/00 | (2017.01) |
| G06T 1/60 | (2006.01) |
| G06K 9/62 | (2006.01) |
| G06F 12/0817 | (2016.01) |
| G06F 12/08 | (2016.01) |

(52) U.S. Cl.
CPC ............ *G06F 3/017* (2013.01); *A61B 5/1116* (2013.01); *A61B 5/1118* (2013.01); *G06F 12/08* (2013.01); *G06F 12/082* (2013.01); *G06K 9/00335* (2013.01); *G06K 9/00342* (2013.01); *G06K 9/6201* (2013.01); *G06T 1/60* (2013.01); *G06T 7/004* (2013.01); *G06T 7/20* (2013.01); *A61B 2562/0219* (2013.01)

(58) Field of Classification Search
None
See application file for complete search history.

(56) References Cited

U.S. PATENT DOCUMENTS

| | | |
|---|---|---|
| 4,144,564 A | 3/1979 | Lamb |
| 4,149,262 A | 4/1979 | Lamb et al. |
| 5,014,327 A | 5/1991 | Potter et al. |
| | (Continued) | |

OTHER PUBLICATIONS

Prokopenko et al., "Optimizing Associative Information Transfer Within Content-addressable Memory," International Journal of Unconventional Computation, vol. 3, Issue 3, Special issue: "Towards Theory of Unconventional Computing," 2008, pp. 273-296.

(Continued)

*Primary Examiner* — Dismery Mercedes
(74) *Attorney, Agent, or Firm* — Yee & Associates, P.C.

(57) ABSTRACT

A method for identifying a motion of interest of an individual. The method includes collecting, at a computer, motion sensor input data of motions of the individual from a motion sensor for an interval of time. The method further includes analyzing, using the computer, the motion sensor input data using an analysis application having a set of classified predetermined motions of interest. The analysis application classifies a movement captured during the interval of time as a motion corresponding to one of a plurality of pre-determined motions of interest based on shared relative attributes. The method further includes generating an output providing notice of an identified predetermined motion of interest to a monitoring system.

20 Claims, 13 Drawing Sheets

(56) References Cited

U.S. PATENT DOCUMENTS

| | | | |
|---|---|---|---|
| 7,591,793 B2 | 9/2009 | Orito et al. | |
| 7,670,303 B2 | 3/2010 | Sato et al. | |
| 8,680,991 B2* | 3/2014 | Tran | G06F 19/3418 340/3.1 |
| 8,914,604 B2* | 12/2014 | Whelan | G06F 17/30286 711/108 |
| 9,298,269 B2* | 3/2016 | Whelan | G06F 3/017 |
| 2006/0267780 A1* | 11/2006 | Adams | A61B 5/1113 340/573.1 |
| 2007/0229663 A1* | 10/2007 | Aoto | G06K 9/00335 348/155 |
| 2008/0214360 A1* | 9/2008 | Stirling | A61B 5/1038 482/9 |
| 2009/0043230 A1* | 2/2009 | Davis-Havill | A61B 5/1118 600/595 |
| 2009/0083207 A1* | 3/2009 | Aparicio, IV | G06N 3/049 706/46 |
| 2009/0319221 A1* | 12/2009 | Kahn | A61B 5/1123 702/141 |
| 2010/0176952 A1 | 7/2010 | Bajcsy et al. | |
| 2010/0217533 A1* | 8/2010 | Nadkarni | A61B 5/1117 702/19 |
| 2011/0066383 A1* | 3/2011 | Jangle | A61B 5/1116 702/19 |
| 2011/0245688 A1* | 10/2011 | Arora | A61B 5/0205 600/483 |
| 2011/0246123 A1 | 10/2011 | Dellostritto et al. | |
| 2011/0275042 A1* | 11/2011 | Warman | A61B 5/1114 434/247 |
| 2012/0116548 A1* | 5/2012 | Goree | A61B 5/1118 700/90 |
| 2012/0146789 A1* | 6/2012 | De Luca | G08B 21/12 340/540 |
| 2012/0214594 A1* | 8/2012 | Kirovski | A63F 13/213 463/36 |
| 2012/0302900 A1* | 11/2012 | Yin | A61B 5/0205 600/484 |
| 2013/0110011 A1 | 5/2013 | McGregor et al. | |
| 2013/0178960 A1* | 7/2013 | Sheehan | G06F 17/40 700/91 |
| 2013/0278501 A1* | 10/2013 | Bulzacki | G06F 3/017 345/157 |
| 2014/0368658 A1* | 12/2014 | Costa | G08B 25/016 348/158 |
| 2015/0262612 A1* | 9/2015 | Kawahara | G06K 9/00342 386/355 |
| 2016/0070958 A1 | 3/2016 | Whelan | |

OTHER PUBLICATIONS

Extended European Search Report, dated Feb. 16, 2016, regarding application No. EP15179309.8, 6 pages.

Office Action, dated Jun. 3, 2016, regarding U.S. Appl. No. 14/573,591, 25 pages.

Final Office Action, dated Sep. 28, 2016, regarding U.S. Appl. No. 14/573,591, 17 pages.

* cited by examiner

| ENTITIES LIKE: NEW OBSERVATION | | |
|---|---|---|
| SCORE | OUTCOME | COMMON ATTRIBUTES |
| 1.00 | reaching | _center_top_fairly_farther_south_fairly_west; _center_middle_fairly_near_south_somewhat_east; _center_middle_moderately_near_south; _center_top_fairly_north; _center_middle_near_south_fairly_west; _center_top_fairly_north; _center_bottom_somewhat_near_north_somewhat_east; _center_top_nearest_south_moderately_east; _center_top_fairly_farther_south_nearest_west; _center_middle_fairly_near_south_somewhat_west; _center_top_moderately_north_fairly_west; _center_top_nearer_south; _center_top_extremely_south_fairly_east; _center_middle_nearer_north_fairly_west; _center_top_somewhat_south; _center_top_fairly_farther_south_somewhat_east; _center_top_fairly_north; _center_top_fairly_far_south_somewhat_east; _center_top_fairly_north; _center_top_fairly_farthest_south_fairly_east; _center_top_extremely_farther_south_moderately_east |

FIG. 10

FIG. 15
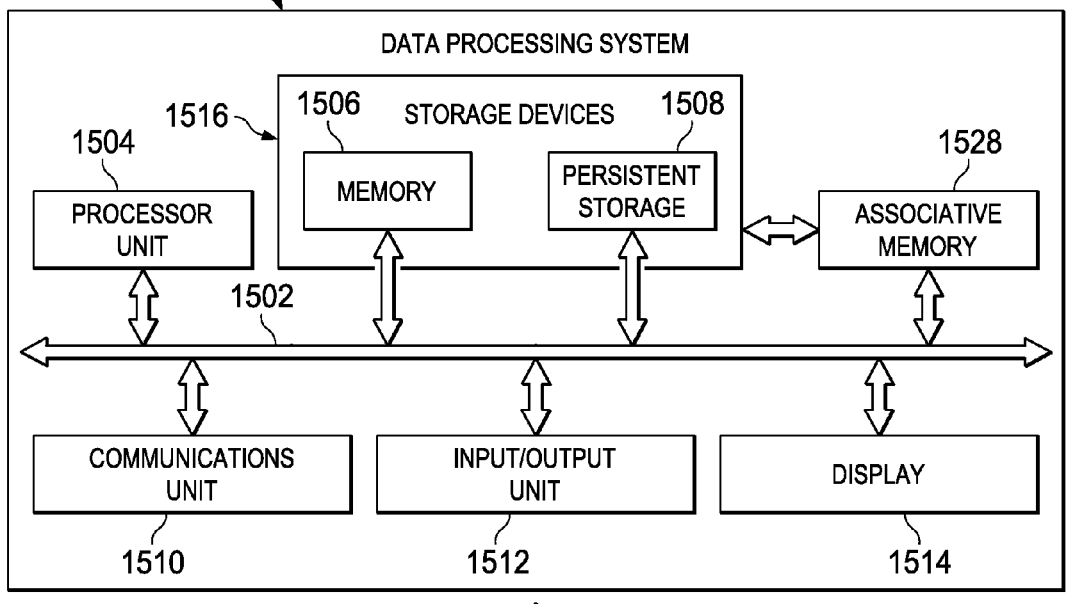
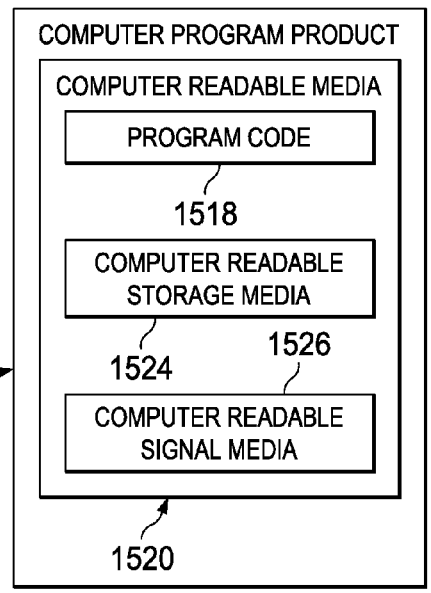

OBTAINING METRICS FOR A POSITION USING FRAMES CLASSIFIED BY AN ASSOCIATIVE MEMORY

BACKGROUND INFORMATION

1. Field

The present disclosure relates to methods and devices for determining for which movements, of a person or object, metrics are to be generated.

2. Background

Classification systems receive data, analyze the data, and then assign the data to a known set using a classifier, where one or more elements of the data correspond to one or more elements of the known set. For example, in a human motion detection classification system, sensors may measure actions of a human. These sensors may input their data to a classification system, which then analyze the data to determine which action the data most resembles. Examples of such a classification may be to classify whether the human sits, stands, walks, holds a phone, bends over, or takes some other action. In another example, a classification system could analyze the input from sensors on an aircraft and then classify some aspect of the aircraft's operation, such as whether the aircraft executes a turn or whether flaps have been deployed.

However, in some cases, measuring additional metrics regarding a person may not be desirable. For example, it may not be desirable to track metrics on the motions of a person due to the unnecessary data that is generated. Thus, methods and devices are desirable that are able to determine for which motions, of a person or object, metrics should be obtained.

SUMMARY

The illustrative embodiments provide for a method for identifying a motion of interest of an individual. The method includes collecting, at a computer, motion sensor input data of motions of the individual from a motion sensor for an interval of time. The method further includes analyzing, using the computer, the motion sensor input data using an analysis application having a set of classified predetermined motions of interest. The analysis application classifies a movement captured during the interval of time as a motion corresponding to one of a plurality of pre-determined motions of interest based on shared relative attributes. The method further includes generating an output providing notice of an identified predetermined motion of interest to a monitoring system.

The illustrative embodiments also provide for an apparatus for identifying a motion of interest of an individual. The apparatus includes a motion sensor and a computer in communication with the motion sensor. The computer is configured to collect motion sensor data from the motion sensor on motions of the individual for an interval of time. The apparatus further includes a non-transitory computer readable storage medium storing an analysis application having a set of classified pre-determined motions of interest. The analysis application is further configured such that when executed by the computer, the analysis application classifies a movement of the individual captured during the interval of time as a motion corresponding to one of a plurality of predetermined motions of interest based on shared relative attributes. The analysis application is further configured, when executed, to generate an output providing notice of an identified predetermined motion of interest to a monitoring system.

The illustrative embodiments also provide for a system. The system includes a kinematic measurement device having one or more sensors configured to detect a plurality of physical positions of a part of an object. The system further includes an associative memory, in communication with the kinematic measurement device, and comprising a plurality of data and a plurality of associations among the plurality of data, wherein the plurality of data is collected into associated groups, wherein the associative memory is configured to be queried based on at least indirect relationships among the plurality of data. The system further includes a processor, in communication with the associative memory and the kinematic measurement device, and configured to receive motion input data of the object from the kinematic measurement device, compare, in conjunction with the associative memory, the motion input data to a plurality of pre-determined motions stored in the associative memory, classify the motion input data as a particular motion selected from the plurality of pre-determined motions, and to notify a monitoring system when the particular motion matches one of a subset of the plurality of pre-determined motions.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 10 illustrates an example of an entity comparison with outcomes as a result category, in accordance with an illustrative embodiment;

FIG. 15 illustrates a data processing system, in accordance with an illustrative embodiment.

DETAILED DESCRIPTION

Figure 1:
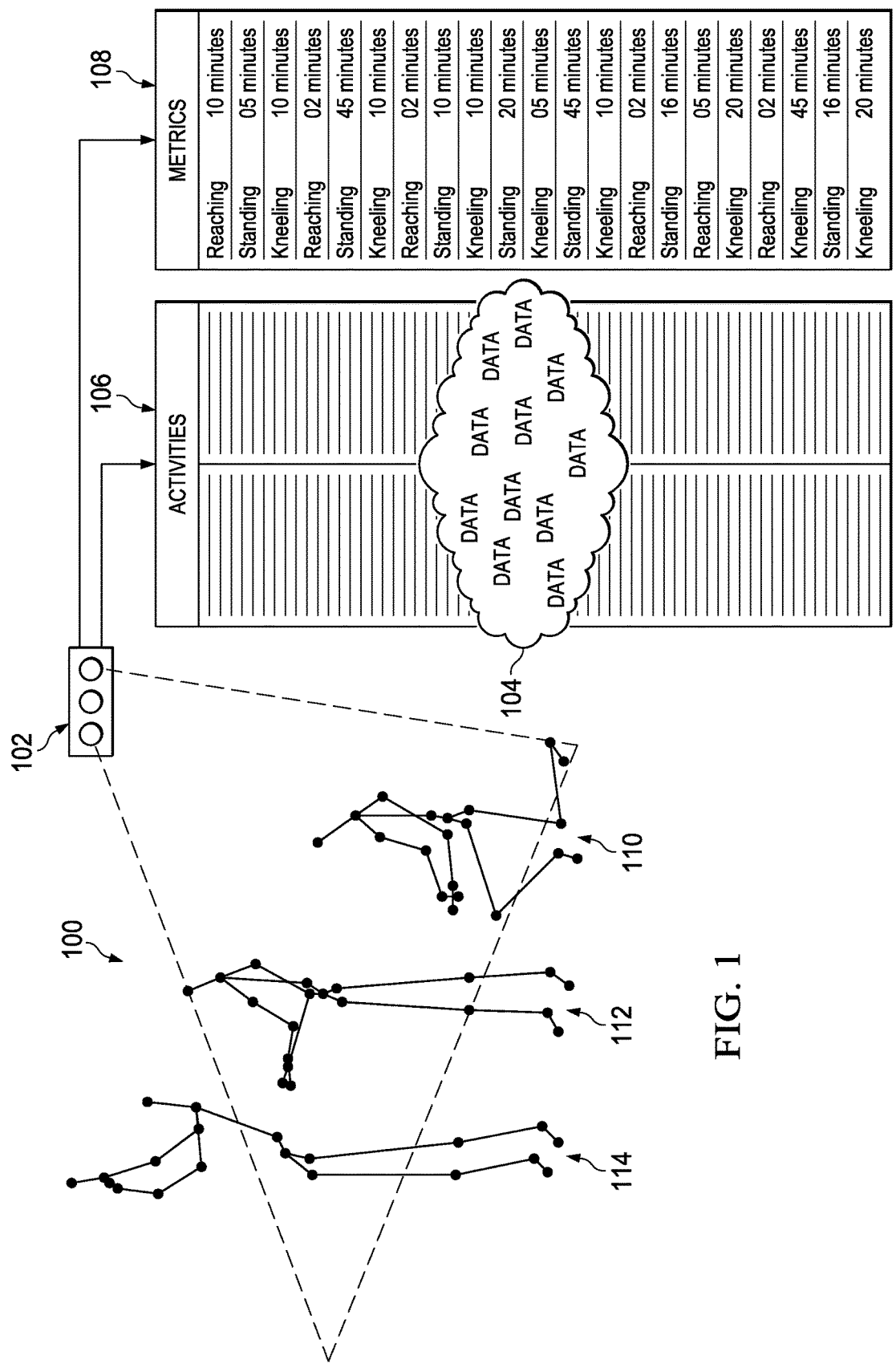
FIG. 1 illustrates one use of a kinematic detection system, in accordance with an illustrative embodiment.

The illustrative embodiments recognize and take into account that obtaining accurate measurements or metrics regarding a particular position of a person is often difficult to gather without having someone physically present to watch. For example, it may be desirable to identify how long an individual maintains an awkward position in order to educate the individual to minimize the potential harm which could occur while the person is in that position. Moreover, many positions can cause harm if done repeatedly or incorrectly. The risk of injury for poor posture may increase within manufacturing facilities, where employees are asked to bend, reach, and extend when installing equipment and parts. One goal of the illustrative embodiments is to help us understand how long employees are in these kinds of positions, in hopes of educating employees as to risky physical behaviors of which they may not be conscious.

The illustrative embodiments also recognize that certain body positions may be hard to identify, due to their nature. Such body positions may be difficult to measure. The illustrative embodiments can single out difficult to measure positions to monitor. The illustrative embodiments may accomplish this goal by capturing difficult to describe behaviors by having a person demonstrate such behaviors and their positions captured. Demonstrated behaviors are used to train a classification system. Thus, a detailed mathematical description of the position may be avoided. This function is described further below.

In the past, monitoring a person's body position in a manufacturing setting involves having someone watch another person as they perform a particular activity. Typically, the observer's role is to collect metrics concerning a certain position as an activity is performed. An example of these metrics is how long a person is in a given type of body position.

This solution does not work very well. First, additional manpower is required to observe, possibly an undesirable amount of additional manpower. Second, because the person being observed often knows they're being observed, the person tends not to carry out the activity in the same manner as if they were alone. Additionally, a human observer is prone to error when observing for long periods of time. Yet further, a human observer may have a cognitive bias which may distort the collected metrics.

Another past monitoring technique was to monitor activities through the use of video cameras. However, this solution still required a human monitor and tended to be less personal than having someone physically present. While cameras can capture a lot of information with regards to specific positions, there still needs to be someone on the other end of the camera to interpret the results. Furthermore, in many situations, the use of video cameras is discouraged or not allowed. Still further, people do not like video cameras watching them, while in the workplace.

The illustrative embodiments recognize these past disadvantages and provide methods and devices for overcoming these disadvantages. Specifically, the illustrative embodiments monitor activities with a motion sensing input device, as opposed to a camera, though the illustrative embodiments could be implemented using a camera if desired. As used herein, a motion sensing input device is an apparatus used to detect the change in position of an object relative to its surroundings or the change in the surroundings relative to an object.

At desired intervals, the motion sensing input device may record a frame or frames of an individual in a certain position and then feeds that information into an associative memory in order to classify the position against previously recorded activities. While the term "associative memory" is defined more formally below, in the context of data processing system 1500 of FIG. 15, briefly an associative memory is a device in which information is collected into associated groups in the interest of gaining new insight based on relationships rather than direct correlation. "Classification" is the task of identifying to which of a set of categories a new observation belongs, on the basis of a training set of data containing observations (or instances) whose category membership is already known. The illustrative embodiments use this information to provide metrics concerning the monitored physical activity of willing users.

One novel aspect of the illustrative embodiments is the ability to use frames collected from a motion sensing input device to detect what position a person is in and determine if metrics for that position should be gathered. After the frames are captured, the illustrative embodiments use an associative memory classification in order to match the frames with a pre-recorded activity. If the classification matches a one of a specific set of positions, metrics pertaining to that position may be generated. Otherwise, monitoring may continue without generating metrics, thereby saving time and data resources.

Thus, the illustrative embodiments use frames, coupled with an associative memory, to identify a particular position and accurately measure it by means of classifying it with pre-recorded activities. The illustrative embodiments do not perform a direct match of a mathematically described position, but instead attempts to match a position's attributes.

Stated differently, a novel aspect of the illustrative embodiments is the ability to interpret a person's position and determine if that position is one that should be measured based on activities previously identified by the user. This ability allows for the quantification of activities which might otherwise be difficult to measure or capture.

The illustrative embodiments have other advantages. For example, the illustrative embodiments may operate in an unobtrusive fashion, being nearly invisible to the participant being observed. While the user should be informed of the observation ahead of time, the operation of the illustrative embodiments may feel less invasive. In another example, the illustrative embodiments make use of inexpensive hardware and centralized software. In another example, the illustrative embodiments are flexible because the illustrative embodiments can function in many situations without being programmed. In another example, the distinctions the illustrative embodiments use to measure different activities can be updated, changed, or improved as needed, possibly in real time. In another example, once configured, no human intervention is needed. The illustrative embodiments may be completely automated.

In another example, the illustrative embodiments are not limited to just monitoring human movement, but could be applied to other non-human movements as well. For example, the illustrative embodiments could be used to track animal movements or the movement of robots, assuming these movements can be detected by an input device.

The illustrative embodiments have the ability to learn by improving its classifications. The illustrative embodiments may replace older and more-cumbersome techniques of monitoring activities. The illustrative embodiments are subject matter independent and universally deployable.

The illustrative embodiments describe a novel application of a motion sensing input device using an associative memory classification rather than the basic licensed core technologies that one uses to accomplish these processes. The illustrative embodiments include the ability to classify an observation, using an example of an associative memory classification. However, the illustrative embodiments could be accomplished with any sort of classification mechanism and is not limited to only the use of an associative memory.

The illustrative embodiments include the ability to detect movements by using an interface to a motion sensing input device. This interface can vary in scope and functionality, but preserves the job of defining the coordinates of a movement in whatever capacity the motion sensing input device can handle.

The illustrative embodiments do not limit what type of activity or position the invention can monitor. The illustrative embodiments do not limit what type of metrics the invention can collect with concerns to said activity or position. The illustrative embodiments do not limit the number of people the invention can monitor with concerns to said activity or position. The illustrative embodiments do not define time constraints on the interval cycle during the monitoring phase.

FIG. 1 illustrates one use of a kinematic detection system, in accordance with an illustrative embodiment. The use of kinematic detection system 102 shown in FIG. 1 does not necessarily limit the claimed inventions, but rather only shows one possible use of the illustrative embodiments. Additional uses for the illustrative embodiments are described below.

In brief summary, the illustrative embodiments monitor activities of one or more individuals 100 with kinematic detection system 102 (which may also be characterized as a motion sensing input device). At set intervals, kinematic detection system 102 records a frame or frames of one or more individuals 100 in certain positions and then feeds that information into associative memory 104 in order to classify that information against previously recorded activities 106. The illustrative embodiments use this information to provide metrics concerning certain activities that are desired to be monitored. In an illustrative embodiment, metrics 108 will be taken only for only certain activities that are considered desirable to monitor.

In more detail, the exemplary use illustrated in FIG. 1 includes using data collected from kinematic detection system 102 to track movements or measured positions of one or more individuals 100. One or more individuals 100 could be a single individual demonstrating multiple positions over time, or could be multiple people in multiple different positions (each of whom is tracked).

The measured positions are fed into associative memory 104 using semantics that associative memory 104 best understands. Thus, for example, kinematic detection system 102 might not send mathematical position data to associative memory 104, but instead send qualitative descriptions of relative positions to associative memory 104. In a more specific example, kinematic detection system 102 could send input that describes the position of the right knee of a person as "somewhat_below_hip." Associative memory 104 can then take this and other qualitative descriptors and compare them to training data, as described further below, to classify the person as kneeling. An example of kneeling is demonstrated by person 110 in FIG. 1. In turn, person 112 demonstrates standing and person 114 demonstrates reaching. In alternative illustrative embodiments, some other intervening hardware or software, or the associative memory itself, could obtain mathematical position or coordinate data from kinematic detection system 102 and translate such data into qualitative descriptors as described above.

In order to reduce processing and data storage requirements, or simply to reduce the amount of reports generated, it may be desirable that only certain positions or movements be monitored. Thus, the illustrative embodiments may be triggered to take metrics 108 on a specific set of positions or movements for which metrics may be desired. Metrics 108 may be, for example, an amount of time a person spends in a particular position, a total amount of time over the course of work day a person spends in a particular person, the longest time spent in a particular position, an average time spent in a particular position, or any other desirable metrics.

For example, without necessarily limiting the claimed inventions, the illustrative embodiments may be used to determine whether a detected movement refers to texting, talking on the phone, walking, bending over, stretching, using a handrail, or any other particular physical activity. The set of possible outcomes may be "texting, talking on the phone, walking, or using a handrail." A determination is made whether the detected movement refers to one member of this set. This determination may be made using an associative memory on the basis of a training set of data containing observations or instances whose category membership is known. In other words, the associative memory has been trained to recognize a particular set of input data as being associated with "texting" or some other position, motion, or activity.

In an illustrative embodiment, metrics 108 are only desired for the activity of "kneeling." So long as the classified position is "kneeling", metrics 108 may then be taken regarding the person's motions over time. Otherwise, metrics 108 are not taken. Alternatively, it may be desirable to take metrics 108 for three activities: standing, kneeling, and reaching, but not for other activities. Again, metrics 108 may be, for example, an amount of time a person spends in a particular position, a total amount of time over the course of a work day a person spends in a particular position, the longest time spent in a particular position, an average time spent in a particular position, or any other desirable metrics.

Turning to the devices used in the illustrative embodiments, kinematic detection system 102 may be any apparatus used to detect changes in position of an object relative to its surroundings or the change in the surroundings relative to an object. In a specific example, which does not necessarily limit the claims, kinematic detection system 102 may be a product that is commercially available off the shelf. Kinematic detection system 102 may be normally used for playing video games, such as in FIG. 3 for example. However, kinematic detection system 102 may be an accelerometer, a camera system, or any other suitable technology for detecting the movement of one or more persons or objects in an area. Thus, for example, kinematic detection system 102 may be used to track positions of a robot. In this case, the illustrative embodiments may determine whether movements of the robot are within design parameters.

Figure 2:
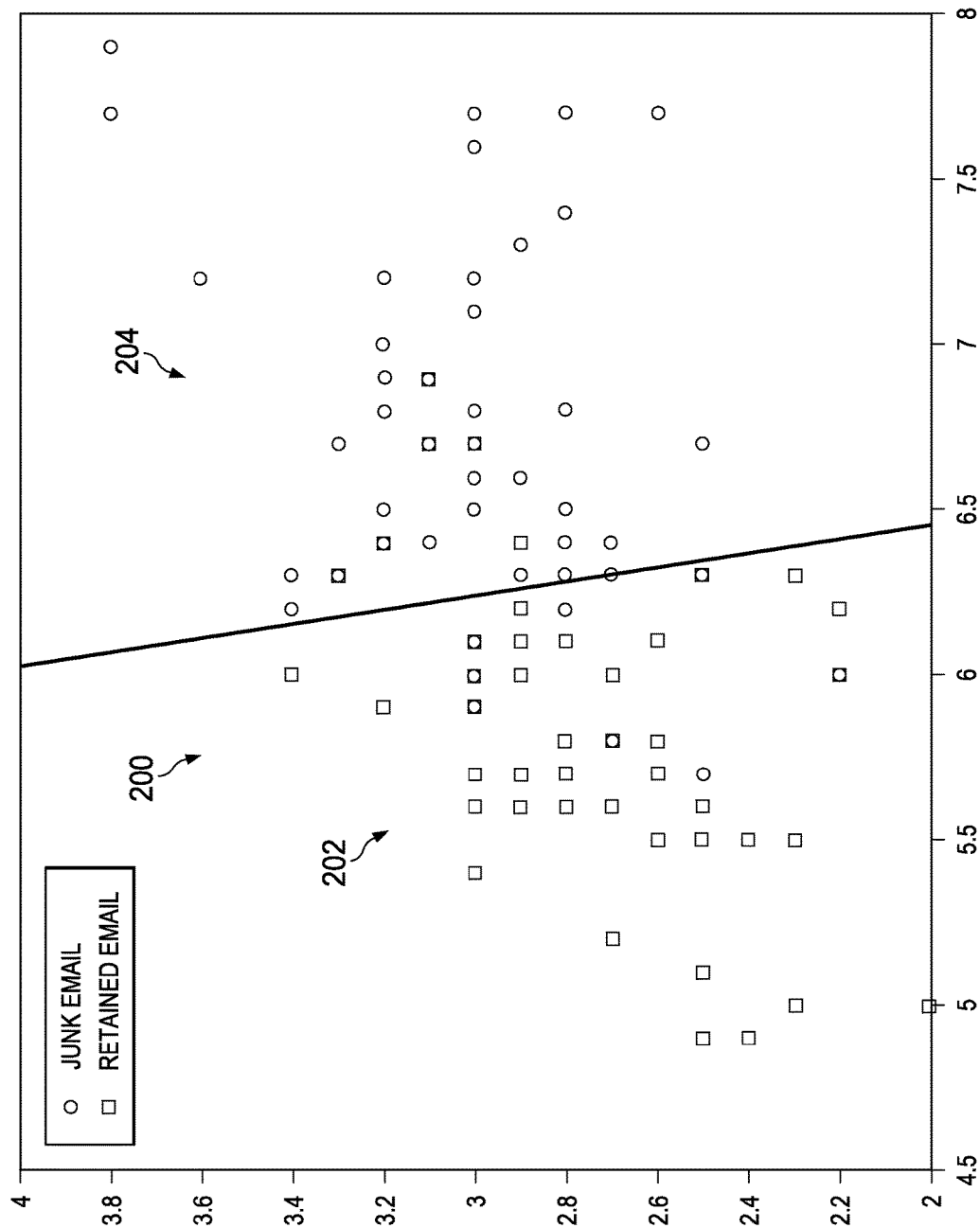
FIG. 2 illustrates an example of a classification system, in accordance with an illustrative embodiment.

FIG. 2 illustrates an example of a classification system, in accordance with an illustrative embodiment. Classification 200 of FIG. 2 illustrates the principles of classification as used herein, not necessarily the illustrative embodiments. In other words, classification 200 illustrates principles of classification that may be used for implementing the illustrative embodiments with respect to determining when to take metrics for particular motions, positions, or activities of users or devices, as described with respect to FIG. 1.

Attention is first turned to what is meant by the term "classification". "Classification," as used herein, is defined as the ability to identify, or the act of identifying, to which group of objects a new observation belongs by comparing a new observation's characteristics to a known set of characteristics. As used in the illustrative embodiments, the known characteristics are established by training the system. "Training the system," as used herein, is defined as providing to the system the characteristics of the known members of the set. Stated differently, training the system instructs the system regarding what a particular position "looks like"; or rather, what the characteristics of the particular position are. When the system is trained, the system may then quickly compare a new observation's characteristics to the set of known members' characteristics, and then equate the new observation as being the one of the known members of the set which most closely matches the new observation's characteristics. As used herein, "the system" or "the illustrative embodiments" refers to a processor, an application specific integrated circuit (ASIC), and/or other physical equipment used or usable to implement the illustrative embodiments, including possibly a non-transitory computer readable storage medium storing program code for implementing the motion capture and classification system described herein.

Returning to FIG. 2, this figure illustrates an example of classification with respect to an email system. In this case, the system classifies incoming email as either retained email or junk email based on certain characteristics. Thus, classification 200 has two known members in the set of known members. These known members are retained email 202 and junk email 204. The system has been trained by establishing first characteristics of retained email 202 and second characteristics of junk email 204. The system is then programmed to compare third characteristics of a new observation, which is an incoming email, to the first characteristics of retained email 202 and the second characteristics of junk email 204. The new observation is then classified as either belonging to retained email 202 or junk email 204.

Again, the characteristics that make up each category, retained email 202 or junk email 204, are already known. For example, retained email 202 typically comes from a recognized sender. Thus, retained email 202 has, as one characteristic, a recognized sender. Other characteristics are also possible. Conversely, junk email 204 typically has a characteristic that it does not come from a recognized sender. Junk email 204 often also has other characteristics, such as the presence of words used in solicitation to sell a product or service. Depending on the number of common matches between characteristics of the new observation and characteristics of the known set of members, the system will establish the appropriate category to place the incoming email.

In the terminology of machine learning, a classification system is considered an instance of supervised learning; that is, learning where a training set of correctly-identified observations is available. The corresponding unsupervised procedure is known as clustering or cluster analysis. Cluster analysis may involve grouping data into categories based on some measure of inherent similarity. An example of measures includes the distance between instances, considered as vectors in a multi-dimensional vector space.

Figure 3:
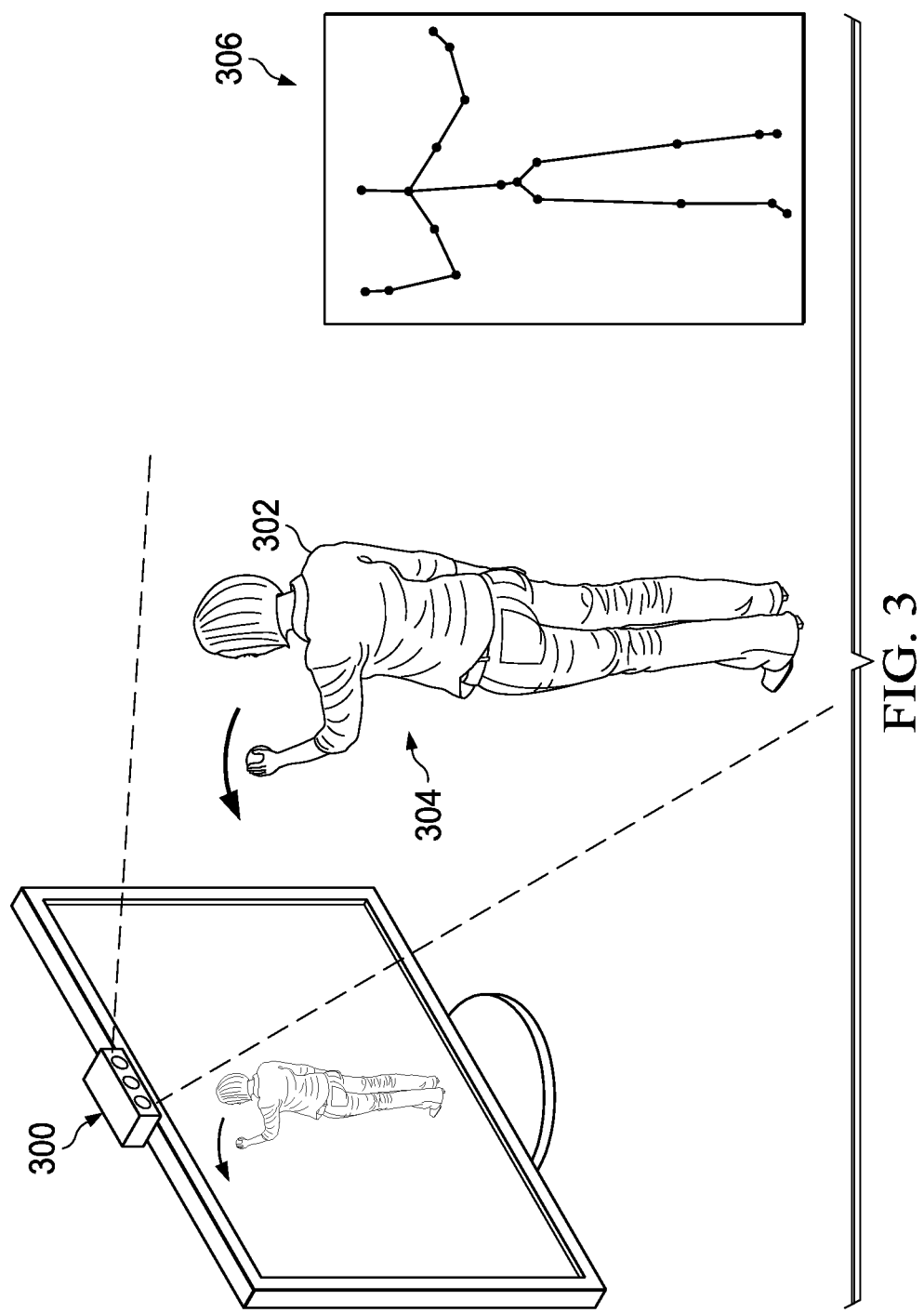
FIG. 3 illustrates an example of a kinematic detection system in use, in accordance with an illustrative embodiment.

FIG. 3 is an example of a kinematic detection system in use, in accordance with an illustrative embodiment. Kinematic detection system 300 may be kinematic detection system 102 of FIG. 1. The movements of user 302 may be classified by the system using a classification system, in a manner analogous to that shown by classification 200 of FIG. 2.

As described above, the illustrative embodiments may use kinematic detection system 300 to movements of user 302. Motion sensing input devices, such as kinematic detection system 102 of FIG. 1, may be used as part of kinematic detection system 300 to detect a change in position of user 302 relative to his or her surroundings 304.

Typically, motion sensing input devices such as kinematic detection system 300 include software which displays the Cartesian coordinates of where the detected movement took place. This display could take the form of a stick person, such as stick person 306, or may not be visually represented at all. In either case, the illustrative embodiments may use the measured coordinates to calculate the movements of user 302.

In order to gauge the subject's movements, the illustrative embodiments may correlate the coordinates of a position shared by all parties, that is to say the illustrative embodiments may compare hand movements to hand movements. The measurements can be further normalized if desired. For example, the illustrative embodiments could also use the distance between parts of the body which are relatively static, such as the center hip to the spine, in normalizing the measurements.

Figure 4:
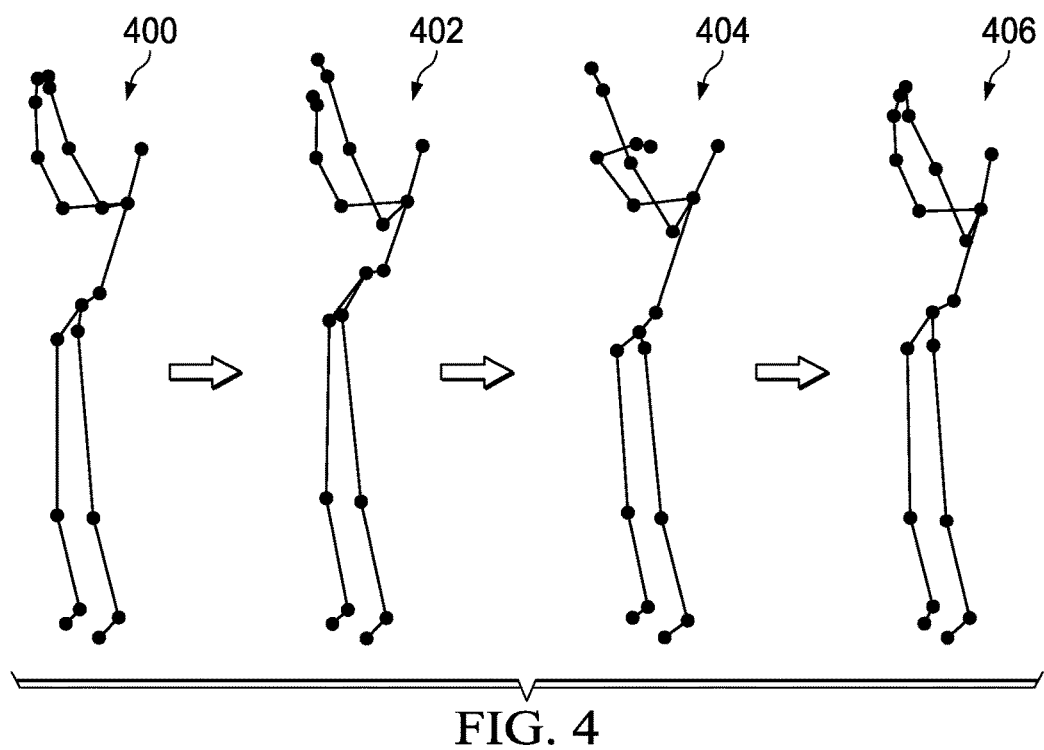
FIG. 4 illustrates an example a pre-recorded activity classified as reaching, in accordance with an illustrative embodiment.
Figure 5:
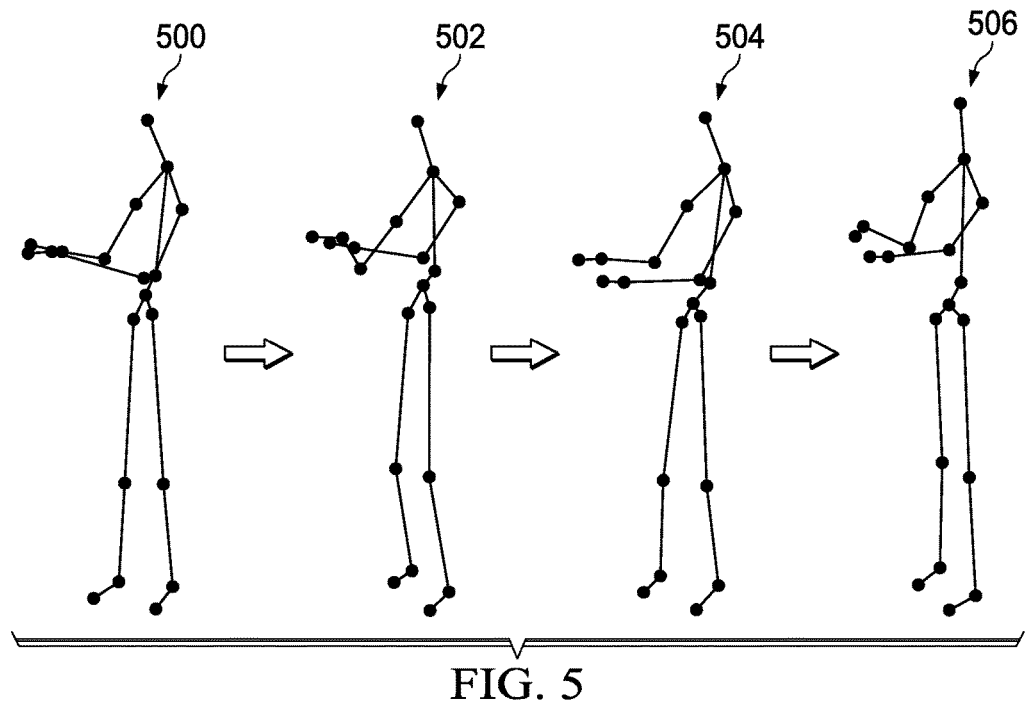
FIG. 5 illustrates an example of a pre-recorded activity classified as standing, in accordance with an illustrative embodiment.
Figure 6:
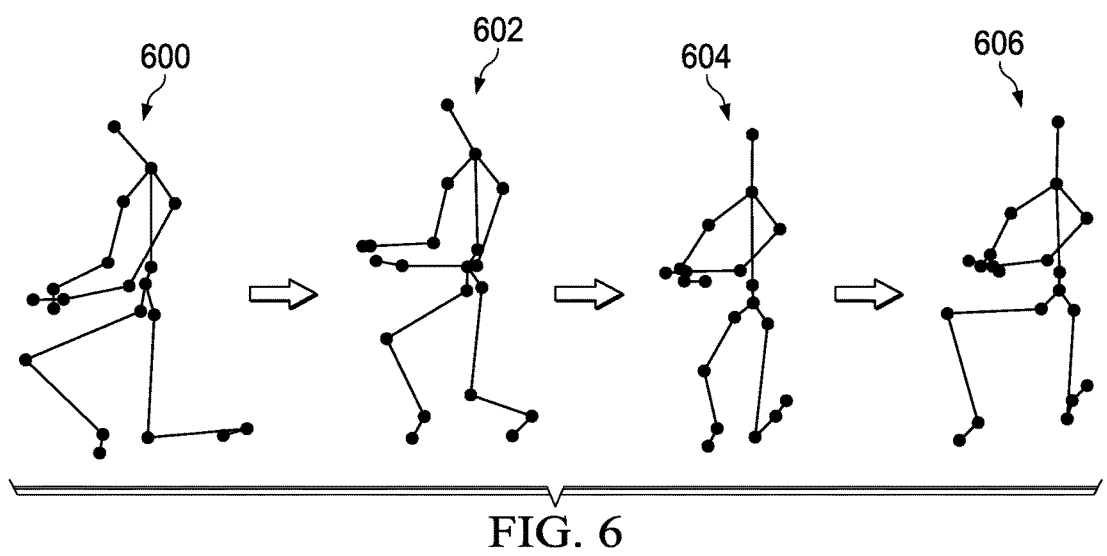
FIG. 6 illustrates an example of a pre-recorded activity classified as kneeling, in accordance with an illustrative embodiment.

FIG. 4, FIG. 5, and FIG. 6 all illustrate examples of pre-recorded activities. Pre-recorded activities are used to train an associative memory, such as associative memory 104 of FIG. 1, so that the associative memory or processor can compare unknown input data to known pre-recorded activities in order to classify the unknown input data as one of the pre-recorded activities. An example of classification is shown in FIG. 2. The input data can be derived from a motion input device, such as kinematic detection system 300 of FIG. 3.

More specifically, FIG. 4 illustrates an example a pre-recorded activity classified as reaching, in accordance with an illustrative embodiment. FIG. 5 illustrates an example of a pre-recorded activity classified as standing, in accordance with an illustrative embodiment. FIG. 6 illustrates an example of a pre-recorded activity classified as kneeling, in accordance with an illustrative embodiment.

In order to improve the quality of matching of unknown input data to a pre-recorded activity, the associative memory can be trained with multiple examples of what constitutes a given activity of interest. Thus, for example, position 400, position 402, position 404, and position 406 are all examples of reaching, even though as shown in FIG. 4 all four positions are somewhat different from each other. Similarly, position 500, position 502, position 504, and position 506 are all examples of standing, even though as shown in FIG. 5 all four positions are somewhat different from each other. Similarly, position 600, position 602, position 604, and position 606 are all examples of kneeling, even though as shown in FIG. 6 all four positions are somewhat different from each other. Note that in the case of FIG. 6, examples of kneeling are taken at different angles relative to the kinematic detection system so that the associative memory can recognize the same position from different angles.

Attention is now turned to what is done once the associative memory has successfully classified an unknown input to one of the positions of interest, such as those shown in FIG. 4 through FIG. 6. A purpose of the illustrative embodiments is to detect if an individual is in a particular position using a kinematic detection system or other motion sensing input device and to gather metrics concerning that position. To achieve this particular purpose, the illustrative embodiments may use an associative memory to store a pre-recorded list of activities. Each activity contains the position or positions for which the user wishes to collect metrics.

Then, during the monitoring phase, an individual's movements may be periodically tested by an associative memory classification to see if they match any of the positions in the pre-recorded activities. If there is a match, the illustrative embodiments collect metrics concerning that position for as long as the individual being monitored maintains the particular position.

The overall process involves a few logical steps. For the purpose of clarity, the following example will describe each step using an example of monitoring an individual installing some equipment, which involves the positions of kneeling, standing, and reaching. The illustrative embodiments will gather metrics with respect to these positions. For this example, the metrics collected will be the duration the individual maintains each position. Note, however, that this specific example does not necessarily limit the claimed inventions or the other illustrative embodiments described herein; many other examples are possible as explained elsewhere herein.

In this particular illustrative embodiment, the first step is to identify the positions for which a user wants to collect metrics. These positions could be part of an overall movement or activity, such as "tying a shoe" or they could be as simple as a stationary position, such as "kneeling".

In either case, in the next, second step the user will demonstrate each move in front of a motion sensor and record them respectively. These recordings will become the basis for the associative memory's classification. For this installation example, the positions for which metrics are to be identified would be kneeling, standing, and reaching. The metrics for these positions would be their durations.

The purpose of recording the activities described in this second step is to tell the classification system which position or positions need metrics collected. During this second step, a user need only demonstrate each activity to the extent that a particular position is captured.

For example, if one desired to gather metrics pertaining to someone reaching, one could demonstrate reaching, by extending one's body a few times in a reaching motion, as conceptualized in FIG. 4. For example, a user could simulate the installation of a luggage rack into an airplane's cabin. The user would repeat this process for the other positions, standing and kneeling, as conceptualized in FIG. 5 and FIG. 6, respectively.

Each activity could be demonstrated a few times, using different people and recorded from different angles. Multiple demonstrations by each of multiple different people will provide the associative memory a rich description for each desired outcome.

Figure 7:
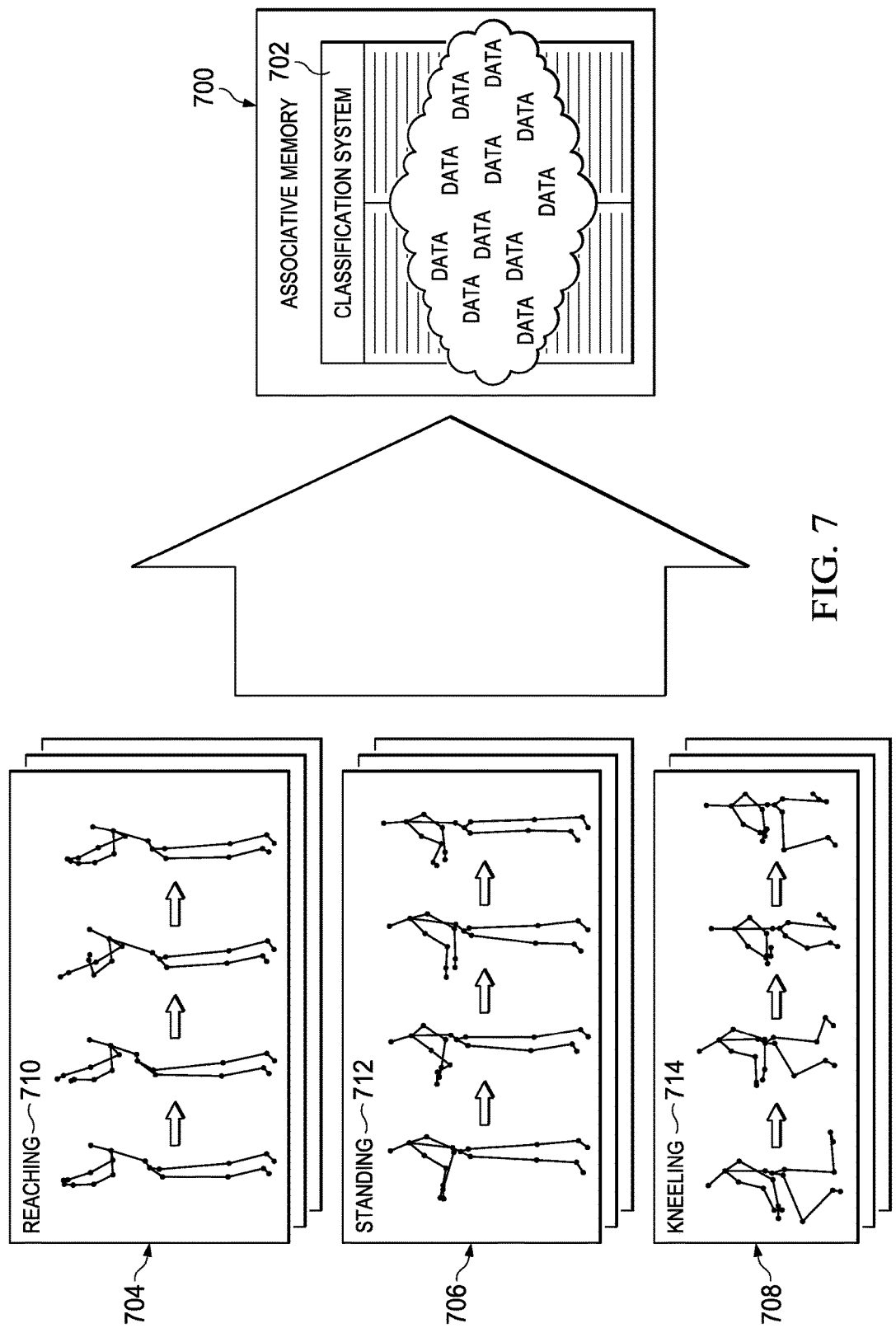
FIG. 7 illustrates an example of inserting activities into a classification system, in accordance with an illustrative embodiment.

FIG. 7 illustrates an example of inserting activities into a classification system, in accordance with an illustrative embodiment. FIG. 7 illustrates a third step in the process started above, which is training the associative memory. The first step (identifying the positions of interest) and the second step (demonstrating examples of positions to train the associative memory) are described above with respect to FIG. 4 through FIG. 6. Associative memory 700 may be, for example, associative memory 104 of FIG. 1. Classification system 702 may be used, for example, to perform classification 200 of FIG. 2. The demonstrated input of reaching 704, standing 706, and kneeling 708 may be, for example, those shown in FIG. 4, FIG. 5, and FIG. 6, respectively.

As stated similarly above, the pre-recorded activities, described in step 2, represent truth data used to train the classification system, which may be classification system 702 of associative memory 700. Each recording is accompanied by an outcome, such as outcome 710, outcome 712, and outcome 714, describing the intent of the movement. During the training phase, associative memory 700 associates each recording's outcome with all the corresponding positions captured, in order to classify the captured corresponding positions. The outcome is what the classification returns, if there is a match. In this case, the outcome is known as the "classifier".

Because the illustrative embodiments capture the positions as a series of movements, the underlying classification is more flexible. This technique allows a match to occur at any point during the activity in order to conclude that the individual was in fact doing the activity. As a result, the illustrative embodiments place the emphasis on the mechanics of the activity, rather than its nuances. Thus, this technique uses less processing power than tracking the precise positions of body parts of the individual. Once the training is complete, the illustrative embodiments insert the captured data into an associative memory, where new observations can then be classified against the collected data to determine a particular outcome and gather metrics if necessary.

For the installation example, the classification system would use the pre-record activities of kneeling, standing, and reaching to train the system. This training is, again, the third step in the process. The complete set would be inserted into classification system 702 of associative memory 700 as demonstrated in FIG. 7.

Figure 8:
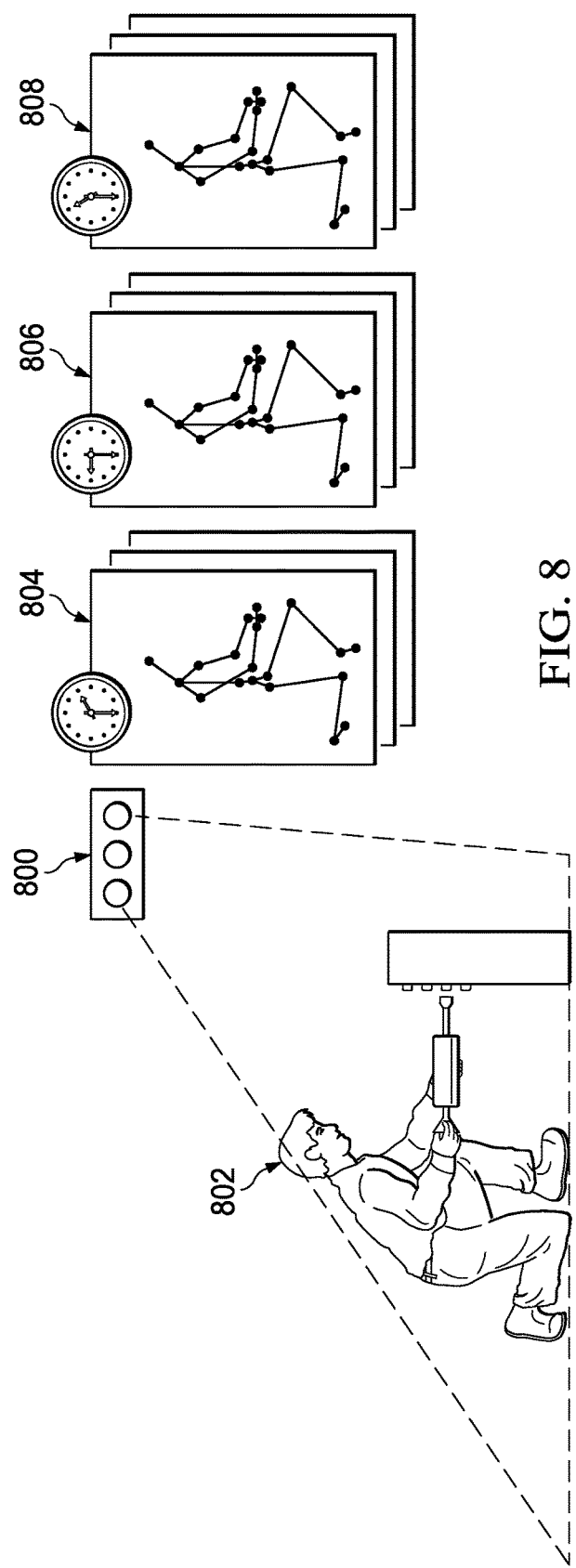
FIG. 8 illustrates an example of monitoring activities, in accordance with an illustrative embodiment.

FIG. 8 illustrates an example of monitoring activities, in accordance with an illustrative embodiment. Monitoring represents a fourth step in the process began above, with the first and second steps described with respect to FIG. 4 through FIG. 6 and the third step described with respect to FIG. 7. Kinematic detection system 800 may be, for example, kinematic detection system 300 of FIG. 3. Kinematic detection system 800 may also be referred-to as a motion sensing input device.

During the fourth step of monitoring, the system periodically collects information from kinematic detection system 800. The system may collect this information as a single frame or multiple frames, depending how the system is configured. The frame or frames provide a current snapshot of what the motion sensor sees at the time the sensor is queried. The goal is to determine whether an individual is in some position, perhaps the pre-identified position for which metrics can be collected.

The fifth step is to identify the captured position using an associative memory classification or some other classification system. The associative memory classifies the position of human 802 by matching the characteristics of an unknown position of human 802 with those characteristics of the known position previously recorded. Note that human 802 need not have been the same person who demonstrated the positions within the training, for example, the pre-recorded activities. In any case, the system will classify the unknown position accordingly. If the classification system does not match any of the pre-recorded activities, then the classification system will return an empty result and accordingly no metrics will be collected.

FIG. 8 shows that human 802 is kneeling. Kinematic detection system 800 will classify human 802 as kneeling. Because the time kneeling (the metric of interest) is to be recorded during the collection of metrics in step 6, the amount of time that human 802 spends kneeling will be tracked. This time need not be contiguous. For example, human 802 could kneel for a time, stand for a time such that metrics are no longer recorded, kneel again during which the time spent kneeling is recorded, reach for a time such that metrics are no longer recorded, and then kneel a third time during which the time spent kneeling is recorded. Thus, FIG. 8 shows three different times during which the amount of time spent kneeling is recorded, time 804, time 806, and time 808.

The collection of metrics continues for as long as the individual being monitored maintains a position of interest. When not collecting, the method returns to monitoring phase, outlined in step 3, and continues until the system is asked to stop.

Figure 9:
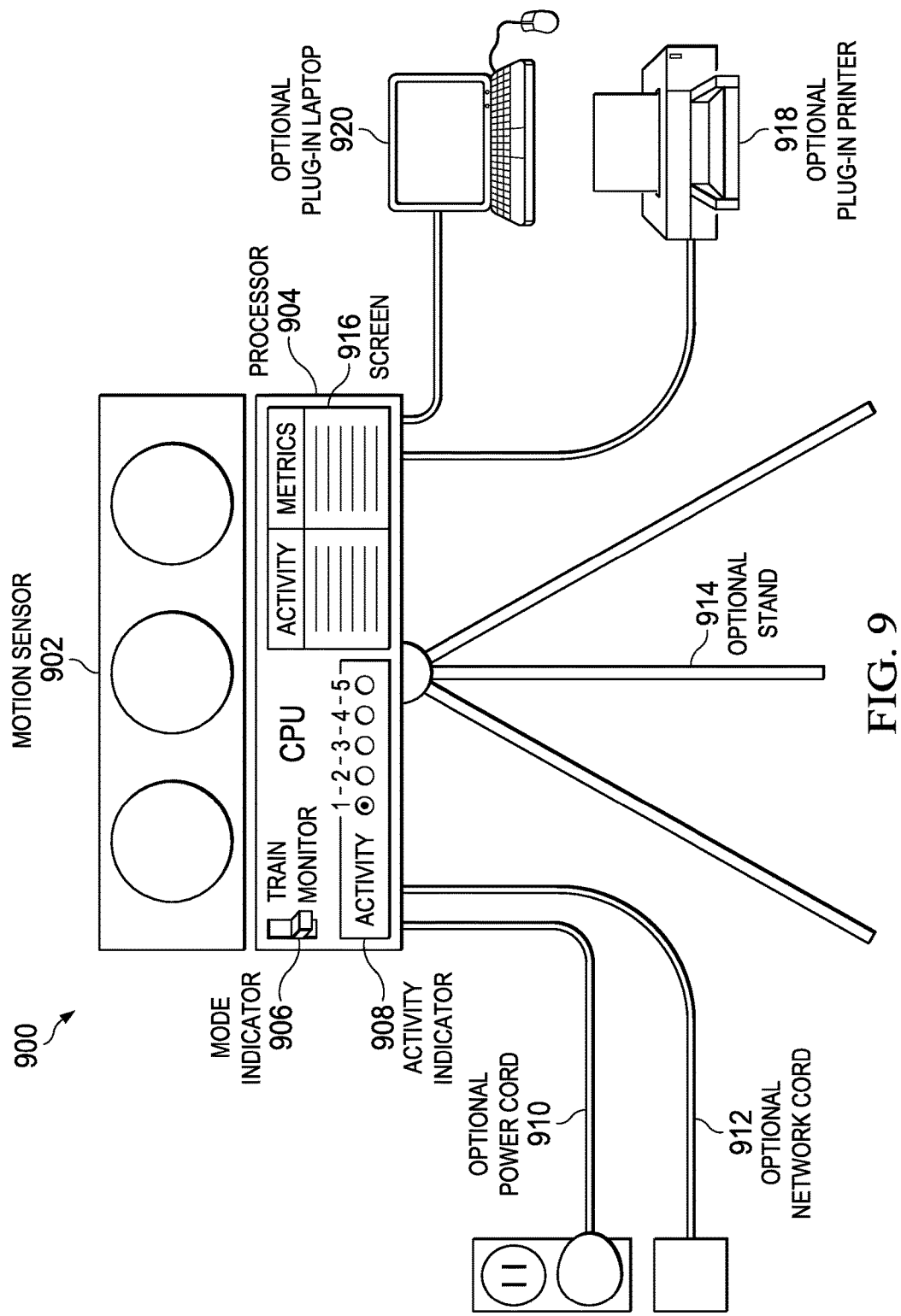
FIG. 9 illustrates an example of a system for collecting metrics using an associative memory, in accordance with an illustrative embodiment.

FIG. 9 illustrates an example of a system for collecting metrics using an associative memory, in accordance with an illustrative embodiment. Kinematic detection system 900 may be, for example, kinematic detection system 102 of FIG. 1 or kinematic detection system 300 of FIG. 3 or kinematic detection system 800 of FIG. 8. The computer or processors used in kinematic detection system 900 may be implemented using data processing system 1500 of FIG. 15.

One possible physical embodiment of the illustrative embodiments is illustrated in FIG. 9, though other physical embodiments are possible. As shown, kinematic detection system 900 uses motion sensor 902 connected to processor 904 that executes the software used to implement the illustrative embodiments, including possibly an associative memory. The computer containing processor 904 may include mode indicator 906 used to indicate whether the device is in training mode or monitor mode. The computer may also include activity indicator 908 to indicate which activity is to be trained.

Kinematic detection system 900 could include optional power cord 910 or a battery. Kinematic detection system 900 could also include optional network cord 912 or a wireless device connecting kinematic detection system 900 to a network. In any case, kinematic detection system 900 may communicate with an associative memory, database, or any other system used to implement the illustrative embodiments. However, in some illustrative embodiments, all the software used may be contained within processor 904 itself. In other illustrative embodiments, the software may instead be embodied as an application specific integrated circuit (ASIC).

Kinematic detection system 900 may include other optional devices or objects. For example, kinematic detection system 900 may include optional stand 914 or be placed somewhere motion sensor 902 could easily observe movements. Kinematic detection system 900 also could include screen 916, or some other output device such as printer or other indicator, used to report or display output. Optionally, plug-in printer 918 may be provided to print out reports, metrics, or other output.

Finally, optional plug-in laptop 920, tablet, mobile phone, or other computer system could be used to help configure or optimize kinematic detection system 900. In addition, plug-in laptop 920 could also be used to update software as desired.

Either processor 904 or plug-in laptop 920 could be used as part of a system for collecting metrics on positions of a person or of an object. Thus, for example, either of processor 904 or plug-in laptop 920 could be used in conjunction with an associative memory connected to either of these devices to monitor a person or object, classify positions of the person or object, and then collect metrics on specific positions of the person or object, as described above.

Stated differently, one possible embodiment of the illustrative embodiments is illustrated in FIG. 9. As shown, kinematic detection system 900 uses motion sensor 902 connected to a CPU device containing software useful for implementing the illustrative embodiments. The CPU device may have mode indicator 906 used to switch modes. For example, the CPU device could be set to training or monitoring. Activity indicator 908 may allow the user to select a predetermined activity for the purpose of identifying which activity the system is training for. For example, these indicators could correspond to a supplementary list which explains which activities are captured.

The illustrative embodiment could include optional power cord 910 or a battery. The illustrative embodiment could also include optional network cord 912 or a wireless device connecting it to a network, so an associative memory, database or any other system credentials could be accessed. However, it is possible to place all the necessary software for the illustrative embodiments within the CPU device itself.

The illustrative embodiments could include optional stand 914 or be placed somewhere else secure. The illustrative embodiments could include a report output, such as screen 906, used for displaying the results of the metrics it gathered. Optional plug-in laptop 920 could be used to help configure, update or optimize the illustrative embodiments. Another option would be to include optional plug-in printer 918, allowing user access to hard copies of reports or metrics on site.

The illustrative embodiments shown in FIG. 9 are not meant to imply physical or architectural limitations to the manner in which different illustrative embodiments may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

FIG. 10 illustrates an example of an entity comparison with outcomes as a result category, in accordance with an illustrative embodiment. Entity comparison 1000 is an example of how an associative memory, such as associative memory 104 of FIG. 1, can classify an unknown input against a set of training positions, as described above with respect to FIG. 4 through FIG. 9.

One possible implementation of the illustrative embodiments is to use an inexpensive motion sensor to capture the activities of interest and a structured query langauge (SQL) database to record them. Then an associative memory could be used to classify new observations, supplied by the motion sensor, against the pre-recorded ones.

For this implementation, a user would setup a pre-defined database and insert the training data, captured by the motion sensor. The training data's outcome would be labeled accordingly, corresponding to each position for which metrics were desired. Then, using an associative memory, a user would ingest this data into the associative memory for the purpose of classifying new observations against it. The data's outcome would be used as the general classifier.

Once ingested, the user could have the system periodically capture movement data from a motion sensor and perform an entity comparison on the captured data to locate other movements like it. The result category of the entity comparison would be set to the "outcome". As a result, the new observation would adopt the outcome of the movement with which it most identifies, as shown in FIG. 10. Thus, for example, set of common attributes 1002 that belong to the outcome 1004 of "reaching" match those attributes of new observation 1006. Score 1008 may be on a scale from zero to one, and represents the closeness of match of the unknown input's attributes to the demonstrated position or activity's attributes. Other score forms or scales could be used for score 1008.

Typically, the results of an entity comparison are an ordered list of entities that are "like" or "similar to" the original or sought entity. An associative memory collects all the matching attributes among these entities to formulate the list. The order of that list depends on the significance of the matching attributes. Additionally, its ranking or score correlates to the number of attributes found.

For a clearer result, the system can perform an entity comparison using a predefined outcome as a result category. The memory can be preconfigured to have each entity associate itself with a particular outcome, such kneeling, standing, or reaching. This technique is an effective way of classifying new observations using a result category, in this case, the outcome as the general classifier.

The illustrative embodiments may be applicable to private companies, governments, or other organizations that are interested in collecting metrics with concerns relating to how employees are performing their daily tasks. The illustrative embodiments allow large scale manufactures to collect such metrics non-invasively.

For example, any company which employs a union contracted staff or is subject to union regulations could utilize the illustrative embodiments. The data is collected without being intrusive and is recorded in a way in which identifying specific individuals is physically impossible. These advantages allow for monitoring and metric gathering in work environments where video monitoring of individuals is prohibited.

The illustrative embodiments provide an efficient way to monitor and measure activities in areas where doing so might be difficult. Furthermore, the illustrative embodiments can provide metrics for positions which are difficult to measure any other way.

The illustrative embodiments provide a cost efficient way of collecting metrics on how long an employee maintains a potentially risky position, thereby helping to avoid increased medical costs. The illustrative embodiments could be used to gather safety metrics, which a company could use to quantify results when trying to measure safety goals. The illustrative embodiments could be used within a factory to benchmark safety goals and showcase examples of good versus bad posture. The illustrative embodiments could be used to measure the frequency of repetitive motion injuries, in hopes of preventing them. The illustrative embodiments could be used to measure how often incorrect ergonomics occur within an office building in hopes of educating employees. The illustrative embodiments can provide metrics on positions which are otherwise impossible to measure. This fact could be utilized in places where supervisors suspect certain manufacturing tasks might be causing harm. Other advantages exist.

Figure 11:
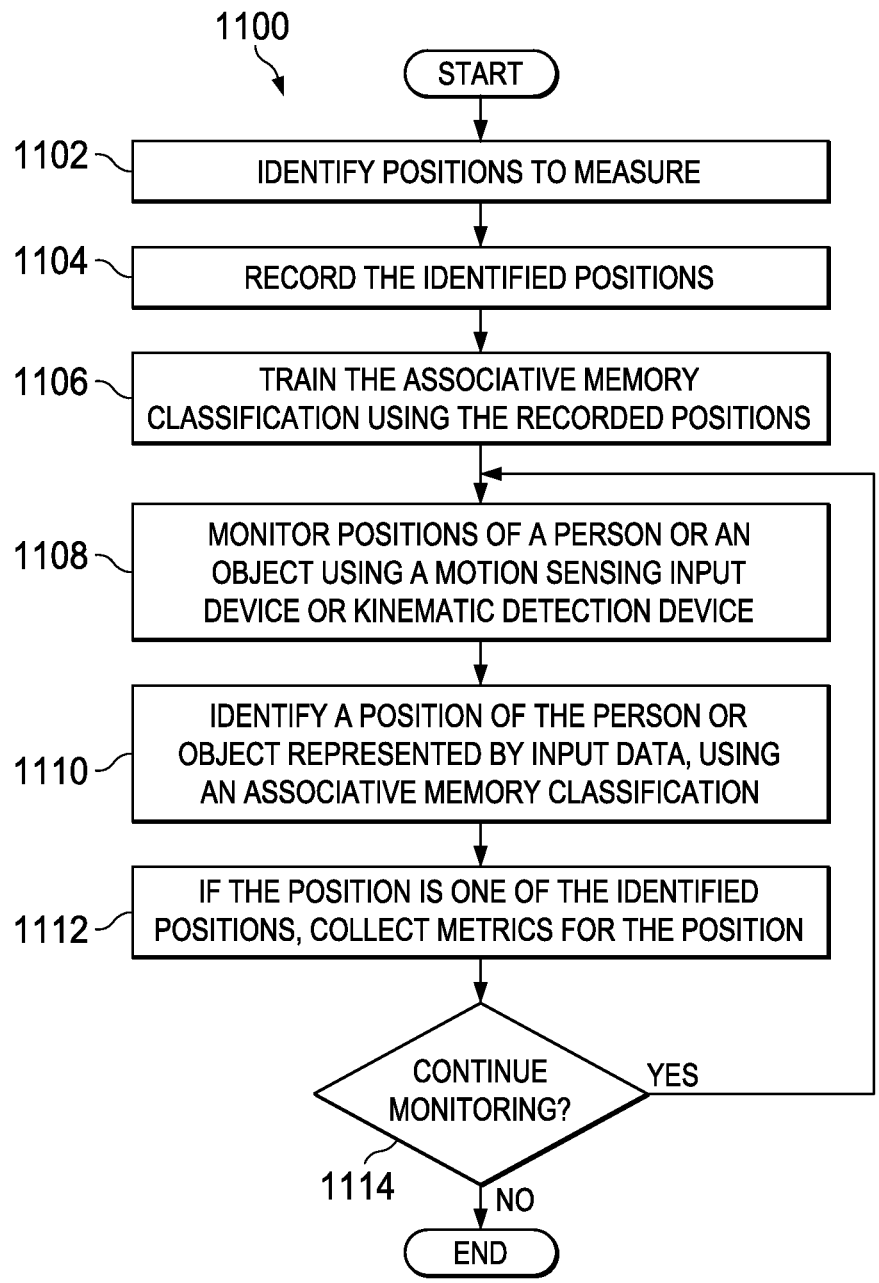
FIG. 11 is a flowchart of a method for identifying a motion of interest of an individual, in accordance with an illustrative embodiment.

FIG. 11 is a flowchart of a method for identifying a motion of interest of an individual, in accordance with an illustrative embodiment. Method 1100 may be a synthesis of the six steps described with respect to FIG. 4 through FIG. 8. However, more or fewer operations may be performed. Method 1100 may be implemented using any of the systems described in FIG. 1 through FIG. 3, as well as FIG. 8 and FIG. 9. For example, reference to "the system" may be to system 900 of FIG. 9, though may refer to another device for carrying out the operations described below.

Method 1100 may begin with the system identifying positions to measure (operation 1102). These positions may be positions or activities of a person or object. The system then records the identified positions (operation 1104). The identified positions may be recorded by a user or an object performing the positions or activities which are to be monitored later.

Method 1100 continues by training the associative memory classification using the recorded positions (operation 1106). The associative memory may be trained by commanding the associative memory to ingest the recorded positions.

Next, the system monitors positions of a person or an object using a motion sensing input device or kinematic detection device (operation 1108). These operations are described with respect to FIG. 8. The system then identifies a position of the person or object represented by input data, using an associative memory classification (operation 1110). This operation is also described with respect to FIG. 8. If the position is one of the identified positions, then metrics are collected for the position (operation 1112). This operation is also described with respect to FIG. 8.

A determination is then made whether to continue monitoring (operation 1114). If monitoring is to continue, then method 1100 returns to operation 1108 and continues. If monitoring is not to continue, then the process may terminate.

The illustrative embodiments shown in FIG. 11 are not meant to imply physical or architectural limitations to the manner in which different illustrative embodiments may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

Figure 12:
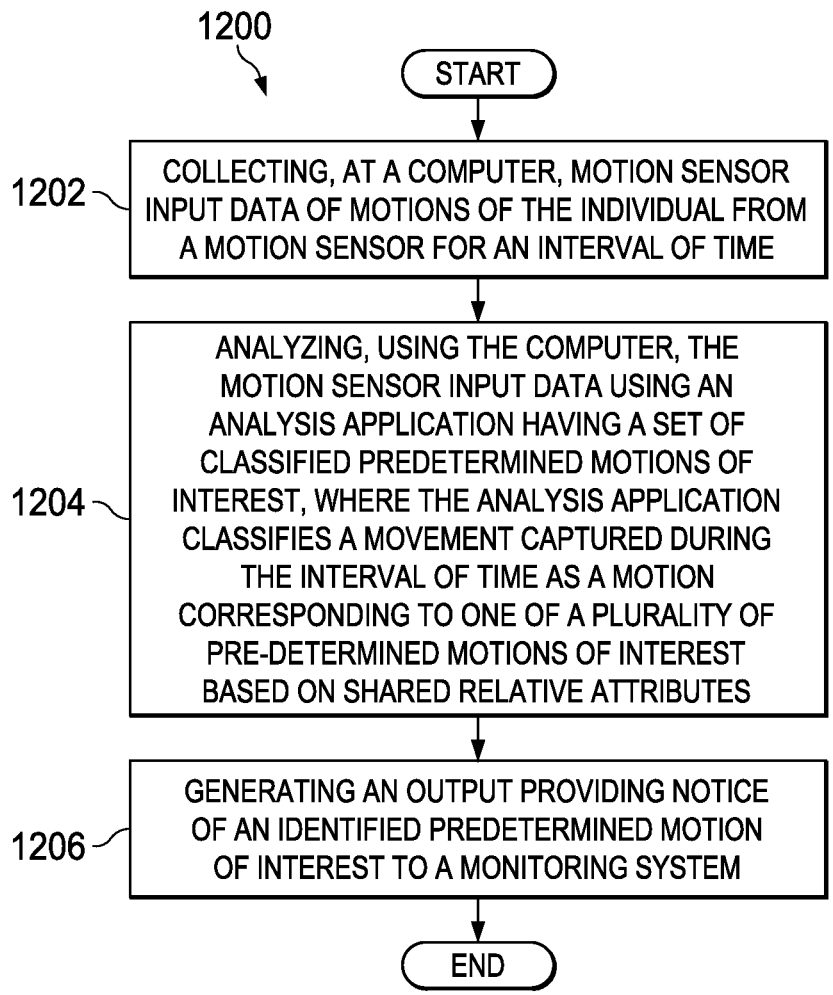
FIG. 12 is another flowchart of a method for identifying a motion of interest of an individual, in accordance with an illustrative embodiment.

FIG. 12 is another flowchart of a method for identifying a motion of interest of an individual, in accordance with an illustrative embodiment. Method 1200 is a variation of method 1100. Thus, method 1100 may be a synthesis of the six steps described with respect to FIG. 4 through FIG. 8. However, more or fewer operations may be performed. Method 1100 may be implemented using any of the systems described in FIG. 1 through FIG. 3, as well as FIG. 8 and FIG. 9. For example, reference to "the system" may be to system 900 of FIG. 9, though may refer to another device for carrying out the operations described below.

Method 1200 may be characterized as a method for identifying a motion of interest of an individual. Method 1200 may include collecting, at a computer, motion sensor input data of motions of the individual from a motion sensor for an interval of time (operation 1202). Next, method 1200 may include analyzing, using the computer, the motion sensor input data using an analysis application having a set of classified predetermined motions of interest, where the analysis application classifies a movement captured during the interval of time as a motion corresponding to one of a plurality of pre-determined motions of interest based on shared relative attributes (operation 1204). Next, method 1200 may include generating an output providing notice of an identified predetermined motion of interest to a monitoring system (operation 1206). The process may terminate thereafter.

However, method 1200 may be varied, and may include more or fewer operations. For example, method 1200 may further include the system generating an alarm output when an identified predetermined motion of interest exceeds a predetermined threshold. Method 1200 may further include, responsive to receiving the notice, collecting metrics on the motion of interest. Method 1200 may further include, responsive to receiving the notice, collecting metrics on additional movements by the individual.

The illustrative embodiments shown in FIG. 12 are not meant to imply physical or architectural limitations to the manner in which different illustrative embodiments may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

Figure 13:
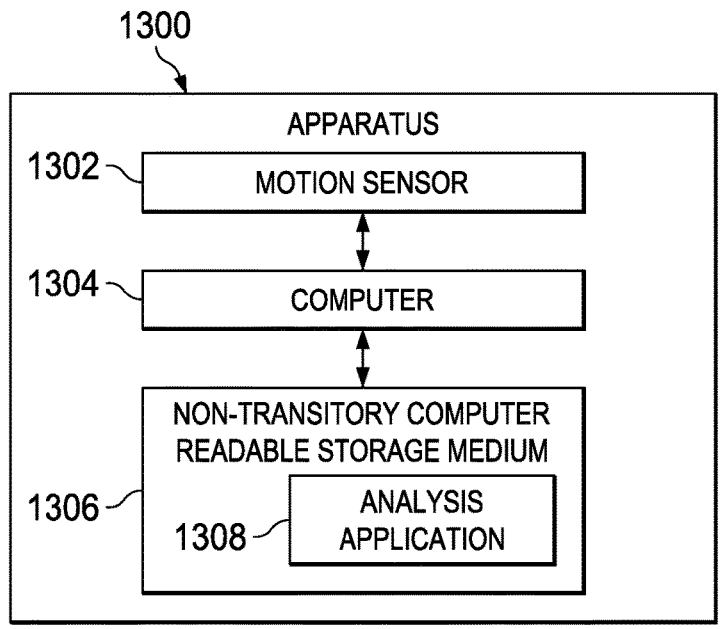
FIG. 13 is an apparatus for identifying a motion of interest of an individual, in accordance with an illustrative embodiment.

FIG. 13 is an apparatus for identifying a motion of interest of an individual, in accordance with an illustrative embodiment. Apparatus 1300 may be a variation of system 900 of FIG. 9. Apparatus 1300 may be characterized as an apparatus for identifying a motion of interest of an individual.

Apparatus 1300 may include motion sensor 1302. Motion sensor 1302 may be non-invasive. Apparatus 1300 may also include computer 1304 in communication with the motion sensor, computer 1304 being configured to collect motion sensor data from motion sensor 1302 on motions of the individual for an interval of time. Computer 1304 may be, for example, data processing system 1500 of FIG. 15.

Apparatus 1300 may also include non-transitory computer readable storage medium 1306 storing analysis application 1308 having a set of classified pre-determined motions of interest. Analysis application 1308 may be further configured such that when executed by computer 1304, analysis application 1308 classifies a movement of the individual captured during the interval of time as a motion corresponding to one of a plurality of predetermined motions of interest based on shared relative attributes. Analysis application 1308 may be further configured, when executed, to generate an output providing notice of an identified predetermined motion of interest to a monitoring system.

Apparatus 1300 may be varied. For example, the processor may be further configured to generate an alarm output when an identified predetermined motion of interest exceeds a pre-determined threshold. Computer 1304 may be further configured, responsive to receiving the notice, to collect metrics on the motion of interest. Computer 1304 may be further configured, responsive to receiving the notice, to collect metrics on additional movements by the individual.

The illustrative embodiments shown in FIG. 13 are not meant to imply physical or architectural limitations to the manner in which different illustrative embodiments may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

Figure 14:
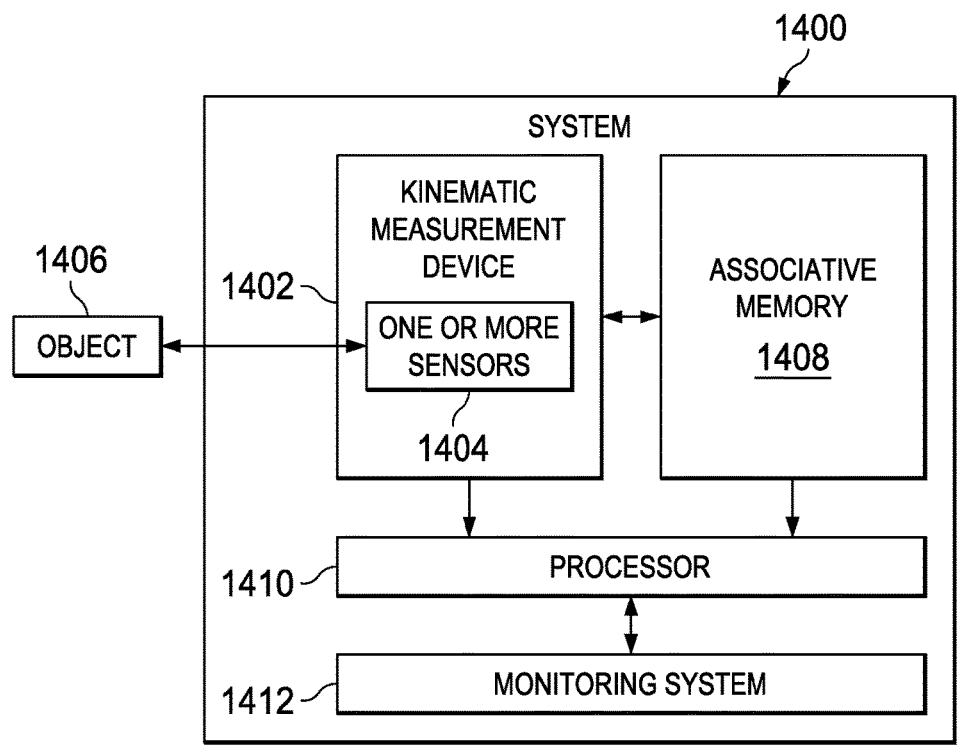
FIG. 14 is a system for notifying a monitoring system when a particular motion matches one of a subset of the plurality of pre-determined motions, in accordance with an illustrative embodiment.

FIG. 14 is a system for notifying a monitoring system when a particular motion matches one of a subset of the plurality of pre-determined motions, in accordance with an illustrative embodiment. System 1400 may be a variation of system 900 of FIG. 9 and system 1400 of FIG. 14.

System 1400 may include kinematic measurement device 1402 having one or more sensors 1404 configured to detect a plurality of physical positions of a part of an object 1406. System 1400 may also include associative memory 1408 in communication with kinematic measurement device 1402. Associative memory 1408 may include a plurality of data and a plurality of associations among the plurality of data. The plurality of data is collected into associated groups. The associative memory is configured to be queried based on at least indirect relationships among the plurality of data.

System 1400 may further include processor 1410. Processor 1410 may be in communication with associative memory 1408 and kinematic measurement device 1402. Processor 1410 may be configured to receive motion input data of the object from kinematic measurement device 1402, compare, in conjunction with associative memory 1408, the motion input data to a plurality of pre-determined motions stored in associative memory 1408, classify the motion input data as a particular motion selected from the plurality of pre-determined motions, and to notify monitoring system 1412 when the particular motion matches one of a subset of the plurality of pre-determined motions. Monitoring system 1412 may be configured to monitor metrics for the pre-determined motions.

For example, processor 1401 may be further configure to cause monitoring system 1412 to measure additional motions of the object when the particular motion matches the one of the subset of the plurality of pre-determined motions. Monitoring system 1412 may be configured to monitor an amount of time the object spends in the pre-determined position.

In another illustrative embodiment, processor 1410 in conjunction with associative memory 1408 may be configured to output an assessment of the additional motions the object. In an illustrative embodiment, the subset may be based on a criteria selected by a user.

In an illustrative embodiment, the object may be a person. In an illustrative embodiment, the subset may be at least one undesirable body position of the person. In an illustrative embodiment, the additional motions may be all motions of the person during an interval of time. In an illustrative embodiment, the additional motions may be only those motions that are within the subset during an interval of time.

In an illustrative embodiment, monitoring system 1412 may monitor motions of an individual body part of the person. In an illustrative embodiment, processor 1410 may be further configured to notify monitoring system 1412 when the motions of the person are no longer in the subset.

In an illustrative embodiment, processor 1410 may be further configured to command monitoring system 1412 to cease monitoring the person when the motions of the person are outside of the subset. In an illustrative embodiment, associative memory 1408 may be configured to be trained to include an additional pre-determined motion within the plurality of pre-determined motions and to include a further motion in the subset of the plurality of pre-determined motions.

Other alternatives are also possible. Thus, the illustrative embodiments shown in FIG. 14 are not meant to imply physical or architectural limitations to the manner in which different illustrative embodiments may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

Turning now to FIG. 15, an illustration of a data processing system is depicted in accordance with an illustrative embodiment. Data processing system 1500 in FIG. 15 is an example of a data processing system that may be used to implement the illustrative embodiments, such as kinematic detection system 102 of FIG. 1, operation 1204 or optional plug-in laptop 920, of FIG. 9, computer 1304 of FIG. 13, processor 1410 of FIG. 14, computer readable media 1520 of FIG. 15, or any other module or system or process disclosed herein. In this illustrative example, data processing system 1500 includes communications fabric 1502, which provides communications between processor unit 1504, memory 1506, persistent storage 1508, communications unit 1510, input/output (I/O) unit 1512, and display 1514.

Processor unit 1504 serves to execute instructions for software that may be loaded into memory 1506. This software may be any of the associative memories described elsewhere herein, or software for implementing the processes described elsewhere herein. Thus, for example, software loaded into memory 1506 may be software for executing method 1100 of FIG. 11, method 1200 of FIG. 12, or for implementing the six steps described above with respect to FIG. 4 through FIG. 8. Processor unit 1504 may be a number of processors, a multi-processor core, or some other type of processor, depending on the particular implementation. A number, as used herein with reference to an item, means one or more items. Further, processor unit 1504 may be implemented using a number of heterogeneous processor systems in which a main processor is present with secondary processors on a single chip. As another illustrative example, processor unit 1504 may be a symmetric multi-processor system containing multiple processors of the same type.

Memory 1506 and persistent storage 1508 are examples of storage devices 1516. A storage device is any piece of hardware that is capable of storing information, such as, for example, without limitation, data, program code in functional form, and/or other suitable information either on a temporary basis and/or a permanent basis. Storage devices 1516 may also be referred to as computer readable storage devices in these examples. Memory 1506, in these examples, may be, for example, a random access memory or any other suitable volatile or non-volatile storage device. Persistent storage 1508 may take various forms, depending on the particular implementation.

For example, persistent storage 1508 may contain one or more components or devices. For example, persistent storage 1508 may be a hard drive, a flash memory, a rewritable optical disk, a rewritable magnetic tape, or some combination of the above. The media used by persistent storage 1508 also may be removable. For example, a removable hard drive may be used for persistent storage 1508.

Communications unit 1510, in these examples, provides for communications with other data processing systems or devices. In these examples, communications unit 1510 is a network interface card. Communications unit 1510 may provide communications through the use of either or both physical and wireless communications links.

Input/output (I/O) unit 1512 allows for input and output of data with other devices that may be connected to data processing system 1500. For example, input/output (I/O) unit 1512 may provide a connection for user input through a keyboard, a mouse, and/or some other suitable input device. Further, input/output (I/O) unit 1512 may send output to a printer. Display 1514 provides a mechanism to display information to a user.

Instructions for the operating system, applications, and/or programs may be located in storage devices 1516, which are in communication with processor unit 1504 through communications fabric 1502. In these illustrative examples, the instructions are in a functional form on persistent storage 1508. These instructions may be loaded into memory 1506 for execution by processor unit 1504. The processes of the different embodiments may be performed by processor unit 1504 using computer implemented instructions, which may be located in a memory, such as memory 1506.

These instructions are referred to as program code, computer usable program code, or computer readable program code that may be read and executed by a processor in processor unit 1504. The program code in the different embodiments may be embodied on different physical or computer readable storage media, such as memory 1506 or persistent storage 1508.

Program code 1518 is located in a functional form on computer readable media 1520 that is selectively removable and may be loaded onto or transferred to data processing system 1500 for execution by processor unit 1504. Program code 1518 and computer readable media 1520 form computer program product 1522 in these examples. In one example, computer readable media 1520 may be computer readable storage media 1524 or computer readable signal media 1526. Computer readable storage media 1524 may include, for example, an optical or magnetic disk that is inserted or placed into a drive or other device that is part of persistent storage 1508 for transfer onto a storage device, such as a hard drive, that is part of persistent storage 1508. Computer readable storage media 1524 also may take the form of a persistent storage, such as a hard drive, a thumb drive, or a flash memory, that is connected to data processing system 1500. In some instances, computer readable storage media 1524 may not be removable from data processing system 1500.

Alternatively, program code 1518 may be transferred to data processing system 1500 using computer readable signal media 1526. Computer readable signal media 1526 may be, for example, a propagated data signal containing program code 1518. For example, computer readable signal media 1526 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 1518 may be downloaded over a network to persistent storage 1508 from another device or data processing system through computer readable signal media 1526 for use within data processing system 1500. For instance, program code stored in a computer readable storage medium in a server data processing system may be downloaded over a network from the server to data processing system 1500. The data processing system providing program code 1518 may be a server computer, a client computer, or some other device capable of storing and transmitting program code 1518.

The different components illustrated for data processing system 1500 are not meant to provide architectural limitations to the manner in which different embodiments may be implemented. The different illustrative embodiments may be implemented in a data processing system including components in addition to or in place of those illustrated for data processing system 1500. Other components shown in FIG. 15 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 1504 may take the form of a hardware unit that has circuits that are manufactured or configured for a particular use. This type of hardware may perform operations without needing program code to be loaded into a memory from a storage device to be configured to perform the operations.

For example, when processor unit 1504 takes the form of a hardware unit, processor unit 1504 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, programmable array logic, a field programmable logic array, a field programmable gate array, and other suitable hardware devices. With this type of implementation, program code 1518 may be omitted because the processes for the different embodiments are implemented in a hardware unit.

In still another illustrative example, processor unit 1504 may be implemented using a combination of processors found in computers and hardware units. Processor unit 1504 may have a number of hardware units and a number of processors that are configured to run program code 1518. With this depicted example, some of the processes may be implemented in the number of hardware units, while other processes may be implemented in the number of processors.

As another example, a storage device in data processing system 1500 is any hardware apparatus that may store data. Memory 1506, persistent storage 1508, and computer readable media 1520 are examples of storage devices in a tangible form.

In another example, a bus system may be used to implement communications fabric 1502 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 1506, or a cache, such as found in an interface and memory controller hub that may be present in communications fabric 1502.

Data processing system 1500 may also include associative memory 1528. Associative memory 1528 may be associative memory 104 of FIG. 1, associative memory 700 of FIG. 1, analysis application 1308 of FIG. 13, associative memory 1408 of FIG. 14, or other associative memories described elsewhere herein, and may have the properties described elsewhere herein. Associative memory 1528 may be in communication with communications fabric 1502. Associative memory 1528 may also be in communication with, or in some illustrative embodiments, be considered part of storage devices 1516. While one associative memory 1528 is shown, additional associative memories may be present.

As used herein, the term "associative memory" refers to a plurality of data and a plurality of associations among the plurality of data. The plurality of data and the plurality of associations may be stored in a non-transitory computer readable storage medium. The plurality of data may be collected into associated groups. The associative memory may be configured to be queried based on at least indirect relationships among the plurality of data in addition to direct correlations among the plurality of data. Thus, an associative memory may be configured to be queried based solely on direct relationships, based solely on at least indirect relationships, as well as based on combinations of direct and at least indirect relationships. An associative memory may be a content addressable memory.

Thus, an associative memory may be characterized as a plurality of data and a plurality of associations among the plurality of data. The plurality of data may be collected into associated groups. Further, the associative memory may be configured to be queried based on at least one relationship, selected from a group that includes direct and at least indirect relationships, or from among the plurality of data in addition to direct correlations among the plurality of data. An associative memory may also take the form of software. Thus, an associative memory also may be considered a process by which information is collected into associated groups in the interest of gaining new insight based on relationships rather than direct correlation. An associative memory may also take the form of hardware, such as specialized processors or a field programmable gate array.

As used herein, the term "entity" refers to an object that has a distinct, separate existence, though such existence need not be a material existence. Thus, abstractions and legal constructs may be regarded as entities. As used herein, an entity need not be animate. Associative memories work with entities.

The different illustrative embodiments can take the form of an entirely hardware embodiment, an entirely software embodiment, or an embodiment containing both hardware and software elements. Some embodiments are implemented in software, which includes but is not limited to forms such as, for example, firmware, resident software, and microcode.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible apparatus that can contain, store, communicate, propagate, or transport the program for use by or in connection with the instruction execution system, apparatus, or device.

The computer usable or computer readable medium can be, for example, without limitation an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or computer usable program code such that when the computer readable or computer usable program code is executed on a computer, the execution of this computer readable or computer usable program code causes the computer to transmit another computer readable or computer usable program code over a communications link. This communications link may use a medium that is, for example without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems or remote printers or storage devices through intervening private or public networks. Non-limiting examples of modems and network adapters are just a few of the currently available types of communications adapters.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for monitoring an individual installing equipment, comprising:
   using a motion sensor to monitor an individual when the individual is installing equipment that involves the positions of kneeling, standing or reaching;
   collecting, at a computer, motion sensor input data of motions of the individual from a motion sensor for an interval of time, for use in determining qualitative descriptions of positions of the individual;
   analyzing, using the computer, the motion sensor input data to classify and identify a position of the individual using an associative memory classification as one of at least standing or kneeling, and to classify a movement captured during the interval of time as a motion corresponding to one of a plurality of pre-determined motions of interest based on shared relative attributes, where the plurality of pre-determined motions includes at least a bending over movement;
   generating an output providing notice of an identified predetermined motion of interest to a monitoring system, and
   monitoring the duration the individual maintains the identified position, to collect metrics on how long the individual maintains a potentially risky position.

2. The method of claim 1, further comprising:
   generating an alarm output when an identified predetermined motion of interest exceeds a predetermined threshold.

3. The method of claim 1 further comprising:
   responsive to receiving the notice, collecting metrics on the motion of interest.

4. The method of claim 1 further comprising:
   responsive to receiving the notice, collecting metrics on additional movements by the individual.

5. An apparatus for identifying a motion of interest of an individual, comprising:
   a motion sensor for monitor an individual when the individual is installing equipment that involves the positions of kneeling, standing or reaching;
   a computer in communication with the motion sensor, the computer being configured to collect motion sensor data from the motion sensor on motions of the individual for an interval of time, for use in determining a plurality of qualitative descriptions of positions of the individual;
   a non-transitory computer readable storage medium storing an analysis application configured such that when executed by the computer, analyzes the motion sensor data to classify and identify a position of the individual using an associative memory classification as one of at least standing or kneeling, and to classify a movement of the individual captured during the interval of time as a motion corresponding to one of a plurality of predetermined motions of interest based on shared relative attributes, where the plurality of pre-determined motions includes at least a bending over movement; and wherein the analysis application is further configured, when executed, to generate an output providing notice of an identified predetermined motion of interest to a monitoring system, and to monitor the duration the individual maintains the identified position to collect metrics on how long the individual maintains a potentially risky position.

6. The system of claim 5, wherein the computer is further configured to generate an alarm output when an identified predetermined motion of interest exceeds a pre-determined threshold.

7. The apparatus of claim 5, wherein the computer is further configured, responsive to receiving the notice, to collect metrics on the motion of interest.

8. The apparatus of claim 5, wherein the computer is further configured, responsive to receiving the notice, to collect metrics on additional movements by the individual.

9. A system comprising:
   a kinematic measurement device having one or more sensors configured to detect a plurality of physical positions of a part of an object;
   an associative memory, in communication with the kinematic measurement device, and comprising a plurality of data and a plurality of associations among the plurality of data, wherein the plurality of data is collected into associated groups, wherein the associative memory is configured to be queried based on at least indirect relationships among the plurality of data; and a processor, in communication with the associative memory and the kinematic measurement device, and configured to use a motion sensor to monitor an individual when the individual is installing equipment that involves the positions of kneeling, standing or reaching; collect motion sensor input data of motions of the individual from a motion sensor for an interval of time, for use in determining qualitative descriptions of positions of the individual; analyze the motion sensor input data to classify and identify a position of the individual using an associative memory classification as one of at least standing or kneeling, and to classify a movement captured during the interval of time as a motion corresponding to one of a plurality of pre-determined motions of interest based on shared relative attributes, where the plurality of pre-determined motions includes at least a bending over movement generate an output providing notice of an identified predetermined motion of interest to a monitoring system; and monitor the duration the individual maintains the identified position, to collect metrics on how long the individual maintains a potentially risky position.

10. The system of claim 9, wherein the processor is further configured to cause the monitoring system to measure additional motions of the object when the particular motion matches the one of the subset of the plurality of pre-determined motions.

11. The system of claim 10, wherein the processor in conjunction with the associative memory is configured to output an assessment of the additional motions the object.

12. The system of claim 11, wherein assessment is based on a criteria selected by a user.

13. The system of claim 10, wherein the object is a person.

14. The system of claim 13, wherein the subset comprises at least one undesirable body position of the person.

15. The system of claim 14, wherein the additional motions comprise all motions of the person during an interval of time.

16. The system of claim 14, wherein the additional motions comprise only those motions that are within the subset during an interval of time.

17. The system of claim 14, wherein an individual body part of the person is monitored.

18. The system of claim 14, wherein the processor is further configured to notify the monitoring system when the motions of the person are no longer in the subset.

19. The system of claim 18, wherein the processor is further configured to command the monitoring system to cease monitoring the person when the motions of the person are outside of the subset.

20. The system of claim 9, wherein the associative memory is configured to be trained to include an additional pre-determined motion within the plurality of pre-determined motions and to include a further motion in the subset of the plurality of pre-determined motions.

* * * * *

UNITED STATES PATENT AND TRADEMARK OFFICE
CERTIFICATE OF CORRECTION

PATENT NO. : 9,619,039 B2
APPLICATION NO. : 14/478475
DATED : April 11, 2017
INVENTOR(S) : Whelan Page 1 of 1

It is certified that error appears in the above-identified patent and that said Letters Patent is hereby corrected as shown below:

In the Claims

Column 23, Line 17, Claim 9 change "movement generate" to -- movement; generate --
Column 24, Line 3, Claim 11 change "motions the object" to -- motions of the object --

Signed and Sealed this
Sixth Day of February, 2018

Joseph Matal
*Performing the Functions and Duties of the*
*Under Secretary of Commerce for Intellectual Property and*
*Director of the United States Patent and Trademark Office*